United States Patent [19]
Pifferi et al.

[11] 3,960,858
[45] June 1, 1976

[54] 3-HETERO ACYL-2,3-BENZOXAZEPINES

[75] Inventors: Giorgio Pifferi, Milan; Amedeo Omodei-Sale', Pavia; Pietro Consonni, Milan, all of Italy

[73] Assignee: Gruppo Lepetit, S.p.A., Milan, Italy

[22] Filed: Nov. 14, 1974

[21] Appl. No.: 523,789

Related U.S. Application Data

[63] Continuation-in-part of Ser. No. 236,222, March 20, 1972, abandoned.

[52] U.S. Cl. .................. 260/247.2 B; 260/268 BC; 260/326.33; 260/333; 424/248; 424/250; 424/274
[51] Int. Cl.² ...................................... C07D 413/06
[58] Field of Search............. 260/247.2, 268, 326.33

[56] References Cited
UNITED STATES PATENTS
3,553,214  1/1971  Martin ................................ 260/244

*Primary Examiner*—Harry I. Moatz
*Attorney, Agent, or Firm*—Theodore Post; C. Kenneth Bjork

[57] ABSTRACT

A new class of 2,3-benzoxazepine compounds of the formula

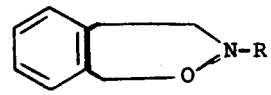

In the formula, R is heterocyclic acyl or heterocyclic acetyl. The compounds have central nervous system and anti-inflammatory activity.

6 Claims, No Drawings

3-HETERO ACYL-2,3-BENZOXAZEPINES

CROSS-REFERENCE TO RELATION APPLICATION

This application is a continuation in part of U.S. Patent Application Ser. No. 236,222, filed Mar. 20, 1972, now abandoned.

SUMMARY OF THE INVENTION

This invention relates to a new class of compounds, 2,3-benzoxazepine derivatives represented by the formula

In the formula, R represents a hetero carbonyl or a hetero acetyl group such as, for example, 1-pyrrolidinylcarbonyl, 4-morpholinylcarbonyl, 4-methyl-1-piperazinylcarbonyl or 4-phenyl-1-piperazinylacetyl.

The process for preparing the basic seven-membered ring fused with the benzene nucleus consists essentially in the condensation and cyclization of o-bromomethylphenethyl bromide with an alkali metal salt of N-hydroxyurethane, e.g., the potassium or sodium salt of N-hydroxyurethane, by mixing the aforesaid reactants together at room temperature or slightly above, advantageously in the presence of an inert organic liquid medium such as a lower alkanol to give 3-carbethoxy-1,3,4,5-tetrahydro-2,3-benzoxazepine, which is hydrolyzed with a strong base, e.g., an alkali metal hydroxide in solution in a lower alkanol, e.g., ethanol to give 1,3,4,5-tetrahydro-2,3-benzoxazepine.

The reaction scheme may be represented as follows:

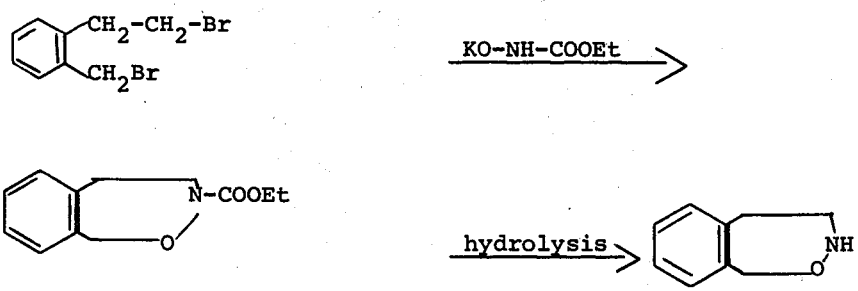

The condensation reaction gives no side-products, since the benzylic bromide atom in (o-bromomethyl)-phenethyl bromide is the more reactive center. The condensation product, 3-carbethoxy-1,3,4,5-tetrahydro-2,3-benzoxazepine, is then hydrolyzed to give the free base by treatment with a strong base such as, for example, an alkali metal hydroxide in a suitable organic solvent, advantageously one of the lower alkanols.

The N-derivatives of 1,3,4,5-tetrahydro-2,3-benzoxazepine are prepared by reactions involving the secondary amino group according to standard procedures. Thus, the syntheses of 3-hetero acetyl derivatives is carried out by condensing the said N-unsubstituted benzoxazepine with an appropriate hetero acetyl chloride in the presence of an acid acceptor such as, for example, triethylamine or an alkali metal hydroxide. When a heterocyclic acyl derivative in which the carbonyl group is directly connected to a nitrogen atom of the heterocyclic ring is desired, a suitable method consists in preparing the 3-chloroformyl derivative of 1,3,4,5-tetrahydro-2,3-benzoxazepine and then reacting this latter compound with a selected nitrogen-containing heterocycle such as, for example, piperazine, morpholine or pyrrolidine.

The new heterocyclic compounds of this invention are solids or liquids which may be distilled under low pressure. The compounds are fairly soluble in most common organic solvents such as the lower alkanols, chlorinated hydrocarbons, dioxane and diisopropyl ether.

The compounds of the invention have central nervous system and anti-inflammatory activity. Their central nervous system activity is essentially myorelaxing, sedative and hypnotic. The myorelaxing activity is evaluated by considering the body tone of the animals treated with compounds of the invention. A decrease in the spontaneous activity of the animals is also observed when the compounds of this invention are administered to mice. This is considered to be related to sedative activity, while impairment of motor coordination and righting reflex are related to hypnotic properties. Another important property shown by the compounds of this invention is the anxiety-relieving effect, which is evaluated on the basis of the secondary conditioned avoidance response.

The favorable biological characteristics of the compounds of this invention are coupled with a relatively low toxicity since the $LD_{50}$ in mice is generally higher than 500 mg/kg i.p. for the compounds of this invention.

In representative experiments, the compound of following Example 6 when tested in rats using the carrageenin-induced edema test at doses between 1/25 and 1/5 of the $LD_{50}$ value showed a decrease of the edema ranging from about 15 to about 50 percent.

The following non-limitative examples describe in detail the manner and process of making and using this invention and the best mode contemplated by the inventors of carrying out the invention.

EXAMPLE 1:

1,3,4,5-Tetrahydro-2,3-benzoxazepine

A:

3-Carbethoxy-1,3,4,5-tetrahydro-2,3-benzoxazepine

A suspension of 210 g. (0.75 mole) of (o-bromomethyl)-phenethyl bromide in 1360 ml. of anhydrous ethanol was treated with 182 g. of 60 percent N-hydroxyurethane K salt (0.75 mole). After stirring at room temperature for two hours until the pH became neutral, a solution of 50 g. of potassium hydroxide 85 percent (0.75 mole) in 680 ml. of ethanol was added and the mixture was heated under reflux for 1.5 hours. The potassium bromide was removed by filtration and the filtrate was concentrated in vacuo. The residue was taken up in diethyl ether, washed with 5 percent aqueous sodium hydroxide and water and dried ($Na_2SO_4$). The solvent was evaporated and the residue was distilled to yield 131 g. (79%) of the title product which boils at 146°–150°C/1 mm. Hg.

Analysis: Calc. for $C_{12}H_{15}NO_3$: C, 65.14; H, 6.83; N, 6.33. Found C, 64.88; H, 6.94; N, 6.33.

B: 1,3,4,5-Tetrahydro-2,3-benzoxazepine

To 100 g (0.45 mole) of 3-carbethoxy-1,3,4,5-tetrahydro-2,3-benzoxazepine in 600 ml. of ethanol, a solution of 32.8 g. of potassium hydroxide in 60 ml. of water was added. After heating at reflux temperature for 30 minutes, the solution was concentrated in vacuo and the residue, dissolved 1000 ml. of diethyl ether, was washed with water and dried. The solution was made acid by adding a diethyl ether solution of hydrogen chloride and the crude precipitate of 1,3,4,5-tetrahydro-2,3-benzoxazepine hydrochloride was collected. Yield 66.3 g., m.p. 173°–176°C.

Analysis: Calc. for $C_9H_{11}NO \cdot HCl$: C, 58.22; H, 6.51; N, 7.55; Cl, 19.10. Found: C, 57.92 H, 6.70; N, 7.40; Cl, 18.75.

The corresponding free base was obtained by treating a cold solution of the crude hydrochloride (66g.) with aqueous sodium carbonate. The base extracted thoroughly with diethyl ether and the extracts, washed with water, were dried and evaporated. The oily residue was distilled to give 49.9 g. (75%) of the title product; b.p. 90° (0.4 mm. Hg.)

Analysis: Calc. for $C_9H_{11}NO$: C, 72.45; H, 7.43; N, 9.39. Found: C, 72.22; H, 7.40; N, 9.54.

EXAMPLE 2:

3-(4-Phenyl-1-piperazinylcarbonyl)-1,3,4,5-tetrahydro-2,3-benzoxazepine

A: 1,3,4,5-Tetrahydro-2,3-benzoxazepine-3-carbonyl chloride

To a solution of 15.9 g. of phosgene in anhydrous toluene a solution of 19.8 g. (0.135 mole) of 1,3,4,5-tetrahydro-2,3-benzoxazepine in the same solvent was added at 0° – 15°C with stirring. After 6 hours it was washed with $H_2O$, dried over $Na_2SO_4$ and the solvent evaporated. Recrystallization from EtOH yielded 22.85 g. (81.5%) of the title compound.

B: 3-(4-Phenyl-1-piperazinylcarbonyl)-1,3,4,5-tetrahydro-2,3-benzoxazepine

To a solution of 4.22 g. (26 mmoles) of N-phenylpiperazine in $CH_2Cl_2$, 4.24 g. (20 mmoles) of 3-chlorocarbonyl-1,3,4,5-tetrahydro-2,3-benzoxazepine was added and the mixture was refluxed for 2 hours, cooled, washed with $NaHCO_3$ and with $H_2O$, dried over $Na_2SO_4$ and the solvent evaporated. Yield 5.5 g. (81.5%), m.p. 123°–125°C, recrystallized from EtOH.

Analysis: Calc. for $C_{20}H_{17}N_3O_2$: C, 71.20; H, 6.87; N, 12.47. Found: C, 71.22; H, 6.90; N, 12.45.

The following compounds wherein R has the designated meaning are prepared from the indicated reactants using procedures as described above.

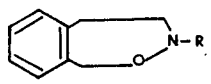

| R | Starting Compounds | B.P., °C/mm Hg or M.P., °C (solvent) | Yield % |
|---|---|---|---|
| 3 | CON⟨⟩N-CH₃ | ⟨⟩N-COCl  HN⟨⟩N-CH₃ | 180/0.1 | 72 |
| 4 | CO-CH₂-N⟨⟩N-⟨⟩ | ⟨⟩N-CO-CH₂Cl  HN⟨⟩N-⟨⟩ | 144–146 (EtOH) | 83.5 |
| 5 | CO-N⟨⟩ | ⟨⟩N-COCl  HN⟨⟩ | 70–72 (Hexane) | 69 |
| 6 | CO-N⟨⟩O | ⟨⟩N-COCl  HN⟨⟩O | 89–92 (diisopropyl ether) | 76 |

The starting material, (0-bromomethyl)phenethyl bromide, is prepared according to the procedure of J. Colonge and P. Boisde, Bull. Soc. Chim. France, 1956: 1337.

What is claimed is:

1. A 1,3,4,5-tetrahydro-2,3-benzoxazepine represented by the formula

wherein R represents 1-pyrrolidinylcarbonyl, 4-morpholinylcarbonyl, 4-methyl-1-piperazinylcarbonyl, 4-phenyl-1-piperazinylcarbonyl or 4-phenyl-1-piperazinylacetyl.

2. A compound of claim 1 which is 3(1-pyrrolidinylcarbonyl)-1,3,4,5-tetrahydro-2,3-benzoxazepine.

3. A compound of claim 1 which is 3-(4-methyl-1-piperazinylcarbonyl)-1,3,4,5-tetrahydro-2,3-benzoxazepine.

4. A compound of claim 1 which is 3-(4-phenyl-1-piperazinylacetyl)-1,3,4,5-tetrahydro-2,3-benzoxazepine.

5. A compound of claim 1 which is 3-(4-morpholinylcarbonyl)-1,3,4,5-tetrahydro-2,3-benzoxazepine.

6. A compound of claim 1 which is 3-(4-phenyl-1-piperazinylcarbonyl)-1,3,4,5-tetrahydro-2,3-benzoxazepine.

* * * * *

UNITED STATES PATENT AND TRADEMARK OFFICE
CERTIFICATE OF CORRECTION

PATENT NO. : 3,960,858
DATED : June 1, 1976
INVENTOR(S) : Giorgio Pifferi et al.

It is certified that error appears in the above-identified patent and that said Letters Patent are hereby corrected as shown below:

Column 1, second typed line, "CROSS-REFERENCE TO RELATION" should read -- CROSS-REFERENCE TO RELATED --.

Column 3, line 17, after the word "dissolved", insert omitted word -- in --.

Column 4, line 55, Claim 2, "3(1-pyrrolidinyl-" should read -- 3-(1-pyrrolidinyl- --.

Signed and Sealed this

Eleventh Day of January 1977

[SEAL]

*Attest:*

RUTH C. MASON
*Attesting Officer*

C. MARSHALL DANN
*Commissioner of Patents and Trademarks*